United States Patent [19]

Lewis et al.

[11] Patent Number: 4,968,742

[45] Date of Patent: Nov. 6, 1990

[54] PREPARATION OF LIGAND-POLYMER CONJUGATE HAVING A CONTROLLED NUMBER OF INTRODUCED LIGANDS

[75] Inventors: Lynette A. Lewis, Goshen; Kin F. Yip, Elkhart, both of Ind.

[73] Assignee: Miles Inc., Elkhart, Ind.

[21] Appl. No.: 118,566

[22] Filed: Nov. 9, 1987

[51] Int. Cl.$^5$ .................. C08F 20/08; C08G 63/48; C08G 63/91; C08L 89/00
[52] U.S. Cl. .................. 525/54.1; 525/54.2; 525/327.4; 525/329.4; 525/329.5; 530/402; 530/403; 530/404; 530/405; 530/406
[58] Field of Search ................ 525/54.11, 54.1, 54.2, 525/327.4, 329.4, 329.5; 530/350, 402, 403, 404, 405, 406

[56] References Cited

U.S. PATENT DOCUMENTS

| | | |
|---|---|---|
| 4,203,893 | 5/1980 | Pery et al. . |
| 4,752,638 | 6/1988 | Nowinski et al. .................. 530/405 |
| 4,762,781 | 8/1988 | Geffard .................. 435/7 |

FOREIGN PATENT DOCUMENTS

| | | |
|---|---|---|
| 1197 | 9/1978 | European Pat. Off. . |
| 28132 | 10/1980 | European Pat. Off. . |
| 77671 | 10/1982 | European Pat. Off. . |
| 94777 | 5/1983 | European Pat. Off. . |
| 142810 | 11/1984 | European Pat. Off. . |
| 149405 | 12/1984 | European Pat. Off. . |
| 178791 | 9/1985 | European Pat. Off. . |
| 246446 | 4/1987 | European Pat. Off. . |
| 251527 | 6/1987 | European Pat. Off. . |
| 2101630 | 7/1982 | United Kingdom . |

OTHER PUBLICATIONS

Makromol. Chem., Rapid Commun. 8, 431–435, (1987), Yokoyama et al., "Preparation of Adriamycin-Conjugated Poly(Ethylene Glycol)–Poly(Aspartic Acid) Block Copolymer".

Previero et al., "Solid Phase Sequential Analysis: Specific Linking of Acidic Peptides by Their Carboxyl Ends to Insoluble Resins", FEBS Letters, vol. 33, No. 1, Jun. 1973, pp. 135–138.

Anderson et al., "The Use of Esters of N-Hydroxysuccinimide in Peptide Synthesis", J. Am. Chem. Soc., 86, May 5, 1964, pp. 1839–1842.

Sutoh et al., "Electron Microscopic Visualization of the SH, Thiol of Myosin by the Use of an Avidin-Biotin System", J. Mol. Biol., (1984), 178, 323–339.

Primary Examiner—Nathan M. Nutter
Attorney, Agent, or Firm—Andrew L. Klawitter

[57] ABSTRACT

A method for chemically coupling a controllable number of ligands, e.g., haptens, to a polymeric material by derivatization of the polymer with an activating agent to introduce a couplable functional group. The derivatization is performed in the presence of a blocking agent which is reactive with the same functionality on the polymer as the activating agent. By reacting the polymer with a mixture of a predetermined ratio of excess amounts of the activating and blocking agents, a controllable number of couplable functional groups are introduced to the polymer for subsequent linkage to the desired ligand. The resulting polymer-ligand conjugates are useful as reagents in immunoassays, particularly immunoturbidimetric assays.

12 Claims, 3 Drawing Sheets

PREPARATION OF LIGAND-POLYMER CONJUGATE HAVING A CONTROLLED NUMBER OF INTRODUCED LIGANDS

BACKGROUND OF THE INVENTION

The present invention relates to methods for coupling ligands such as bindable biological substances to polymeric materials. The resulting ligand-polymer conjugates are particularly useful as reagents in binding assays, e.g., immunoassays. More particularly, the invention concerns such coupling methods wherein steps are taken to control in a reproducible manner the number or density of ligands that become linked to the polymeric material.

There is a continuing need for improved methods of chemically coupling ligands to polymeric supports, particularly in the preparation of immunoassay reagents. Analytical performance is often dependent upon how well characterized and reproducible such reagents can be prepared. This is particularly true for the agglutinator reagent in an immunoturbidimetric assay.

The typical protocol for performing an immunoturbidimetric assay involves setting up a competitive binding reaction between the analyte of interest in the test sample and the agglutinator reagent for binding to antibody against the analyte. The agglutinator reagent comprises a polymer support bearing multiple ligands capable of binding with a particulate reagent bearing anti-analyte antibody. Binding between multiple agglutinator reagent molecules and multiple anti-analyte particles produces an agglutination that is detectable by turbidimetry. Since analyte in the sample competes with this agglutination reaction, as analyte concentration increases, the turbidity of the reaction mixture decreases.

Assay performance of the immunoturbidimetric system is dependent upon the consistency of the agglutinator reagent. If the number of ligand moieties coupled to individual polymers varies widely in the reagent population, the size and rate of formation of light scattering centers produced upon agglutination will similarly vary widely. Such variance can introduce a significant error factor in the precision of the assay. Likewise assay sensitivity is affected by variability in the agglutinator reagent. If the average number of ligands per polymer is low, the maximum agglutination in the absence of analyte is of limited detectability. On the other hand, if the ligand density is too high, it becomes difficult for low levels of analyte to effectively compete for binding to the antibody reagent.

The prior art attempts to control the number or density of ligands coupled to polymer supports have depended essentially on the ability to control all reaction conditions affecting the coupling reaction such as reactant concentrations and purity, temperature, pH, and time of reaction. The ability to control so many different aspects of the coupling process is not practical considering the types of polymeric materials that are conventionally used. Natural biopolymers such as bovine serum albumin as well as synthetic materials have been used for the preparation of multivalent ligand-polymer conjugates. However, such polymeric materials generally have limited available coupling sites as well as reactivity that is sensitive to slight changes in coupling conditions.

SUMMARY OF THE INVENTION

In accordance with the present invention there is provided a method for chemically coupling a controllable number of ligands to a polymeric material. A central step in the method is the derivatization of a repeating functional group on the polymeric material to introduce a controllable proportion of a second functional group which ultimately serves as the point of coupling of the desired ligand moiety. Such controlled introduction of the second functional group is obtained by reacting the polymeric material with a mixture of a predetermined ratio of excess amounts of (1) an activating agent which is reactive with the repeating functional group on the polymer to form a covalent bond and which comprises the second functional group, and (2) a blocking agent which also is reactive with the repeating functional group on the polymer but which does not comprise the second functional group or any equivalent reactive group.

The extent to which the repeating functional groups on the polymeric material are modified to the second, ligand-couplable, group is a reproducible function of the predetermined ratio of the activating and blocking agents in the reaction mixture. The activating and blocking agents compete for reaction with the polymer functional groups. Where the activating agent is successful in coupling to a particular functional group on the polymer, the ligand-couplable second functional group becomes extended therefrom and available for coupling to the ligand. On the other hand, where the blocking agent is successful in coupling, the polymer functional group is modified to be unreactive with the activating agent without introducing the ligand-couplable second functional group. The use of excess amounts of the activating and blocking agents dictates that the ratio of successful couplings with the activating and blocking agents, respectively, is substantially independent of any other reaction condition and therefore is highly reproducible within narrow limits.

A number of advantages result from the ability of the present method to afford control of the number, and therefore the density, of ligands introduced onto the polymeric material. A principal advantage is simply the reproducibility with which the ligand-polymer conjugate can be prepared, particularly in commercial manufacture. When used as an immunoassay reagent, the ligand density on the conjugate can be optimized for assay performance. As a result, the assay exhibits improved sensitivity and precision due to the ability to attach a controllable high density of ligand on the polymer. This leads to enhanced signal production without substantially affecting the ability of analyte to effectively compete with the ligand-polymer conjugate for binding to antibody.

DESCRIPTION OF THE PREFERRED EMBODIMENTS

Figure 1:
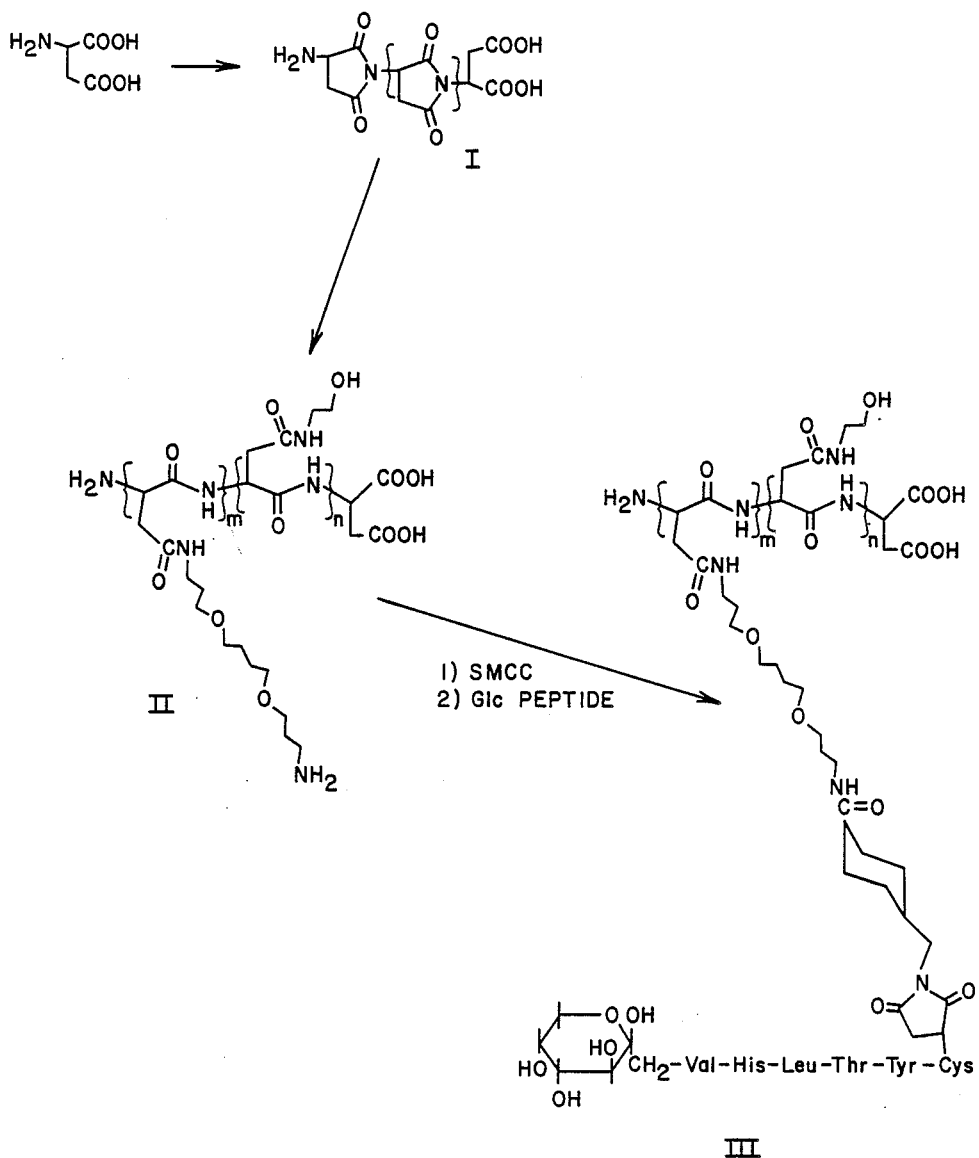
FIG. 1 is a flow diagram of the embodiment of the present method that is described in the Examples below. Poly(aspartic acid) (I) is prepared and reacted with a diamine activating agent and a monoamine blocking agent to form an amino-functionalized polymer (II) in which m monomeric units are amino-functionalized and the remaining n monomeric units are blocked. Further activation of the amino groups and condensation with a desired ligand (Glc-peptide) yields the ligand-polymer conjugate (III) of controlled ligand density m.
Figure 2:
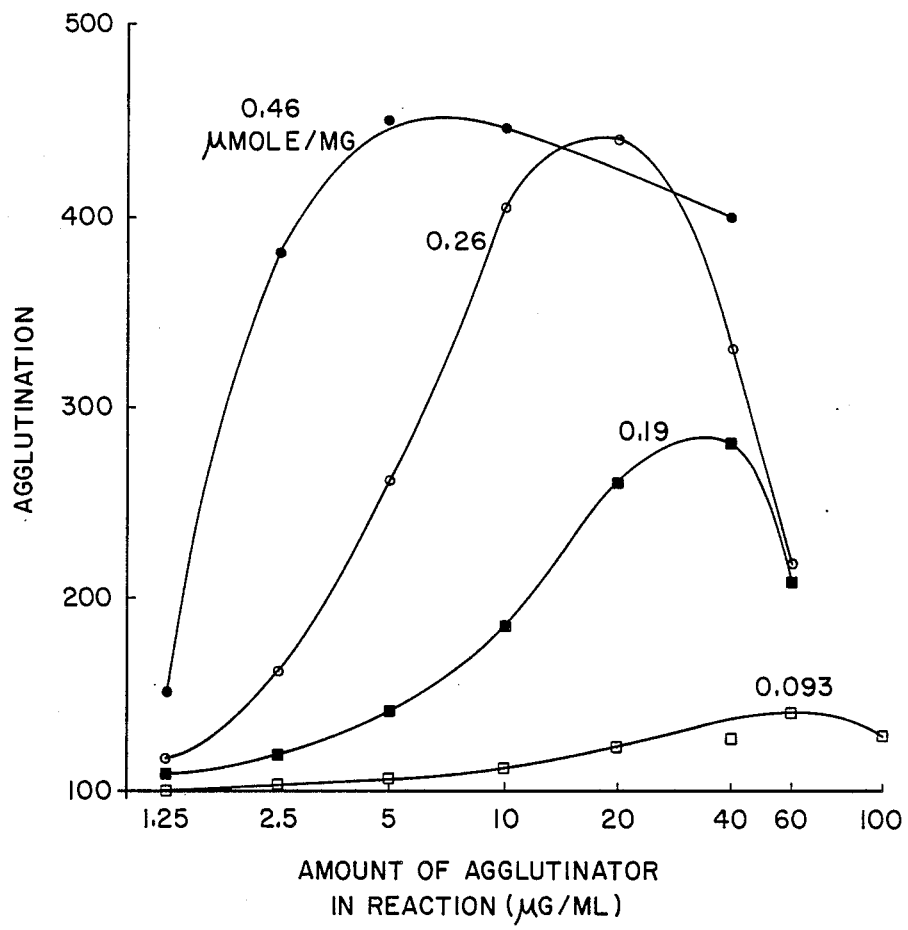
FIGS. 2 and 3 are graphical presentations of data showing the relationship between ligand density on the polymer and performance in an agglutination-based immunoassay system.
Figure 3:
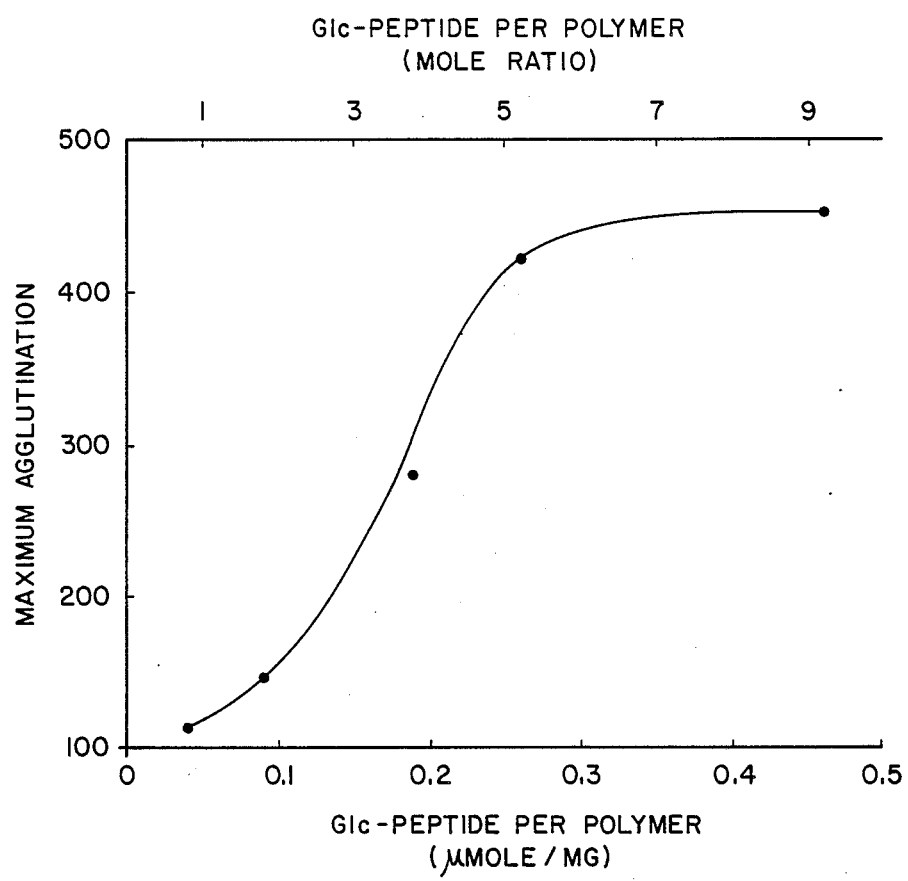

The starting polymeric material may be of any desired chemical composition and any desired form provided that it comprise a derivatizable repeating functional group. Representative functional groups for this purpose include, without limitation, amino, carboxyl, hydroxyl, epoxy, halide, sulfhydryl, hydrazido, azido and diazonium groups. The polymer can be a homopolymer or a copolymer, and in the latter case will preferably have a high proportion of monomeric units bearing the derivatizable functional group. Generally, the polymeric material will be water soluble since the primary use of the ligand-polymer conjugate is as a reagent in immunoassays performed on aqueous test samples. The polymeric material may, however, be insoluble and of any desirable shape and of essentially any desired molecular weight. For example, the polymer may be a solid surface such as the wall of a reaction vessel, test tube, or microtiter well, or a bead or particle.

The present invention is particularly applicable to the coupling of ligands to water soluble or suspensible polymer materials. Accordingly, the polymer will generally have a molecular weight between about 5,000 and about 500,000 daltons, more usually between about 10,000 and about 50,000 daltons. Polymers particularly suited for use in the present method include, without limitation, the water soluble forms of poly(aspartic acid), poly(glutamic acid), poly(methylvinylether-maleic anhydride) (sold under the trademark Gantrez, GAF Chemical Co., Wayne, N.J. U.S.A.), poly(acrylic acid), poly(acrylic-acylamide), and carboxymethylcellulose.

The linking reaction between the polymer and the activating and blocking agents can be selected essentially on the basis of convenience. Representative examples of useful linking reactions are condensation of amino and carboxyl groups, alkylation of amino or sulfhydryl groups with alkyl halides, condensation of hydrazido and carboxyl groups, condensation of hydroxyl and carboxyl groups, coupling of amino and diazonium groups, and coupling of epoxy and amino or sulfhydryl groups. It will generally be preferred, but is not required, that the respective group on the activating and blocking agents which reacts and couples covalently to the polymer be the same chemical group. Where these reactive groups are different, their relative reactivities with the derivatizable repeating group on the polymer will be constant and will play a role, along with the ratio of reactants, in the density of functionalization of the polymer that takes place in the activation/blocking reaction.

The ligand-couplable functional group introduced to the polymer by the activating agent will be selected to provide a relatively selective site for coupling of the ligand. Such functional group will be, for example, an amino, carboxyl, hydroxyl, epoxy, halide, sulfhydryl, hydrazido, azido, or diazonium group. Accordingly, the blocking agent will be selected not to comprise a functional group that has any substantial reactivity or equivalence to such ligand-couplable group. It will be understood that a wide variety of activating/blocking agent pairs are useful in the present invention. Without suggesting any limitation of the principle of the present invention, representative examples of such pairs are provided in the indicated list herein.

| LIST OF REPRESENTATIVE ACTIVATING/BLOCKING AGENT PAIRS | | |
|---|---|---|
| Polymer Functionality | Activating Agent | Blocking Agent |
| Carboxyl | $NH_2-R-NH_2$ | $NH_2-R'$ |
| Amino | $HOOC-R-COOH$ | $HOOC-R'$ |
| Sulfhydryl | $ICH_2\overset{O}{\overset{\|}{C}}-R-\overset{O}{\overset{\|}{C}}CH_2I$ | $ICH_2\overset{O}{\overset{\|}{C}}-R'$ |
| Sulfhydryl | (maleimide)N—R—N(maleimide) | (maleimide)N—R' |
| Sulfhydryl | (maleimide)N—R—N(maleimide) | $ICH_2\overset{O}{\overset{\|}{C}}R'$ |
| Epoxy | $NH_2-R-NH_2$ or $HS-R-SH$ | $NH_2-R'$ or $HS-R'$ |
| Hydroxyl | $HOOC-R-COOH$ | $HOOC-R'$ |
| Hydroxyl | $Cl-R-Cl$ | $Cl-R'$ |
| Chloromethyl | $H_2N-R-NH_2$ | $NH_2-R'$ |
| Hydrazido | $HOOC-R-COOH$ | $HOOC-R'$ |
| Diazonium | $H_2NR-NH_2$ | $NH_2-R'$ |

In the list of representative pairs of activating and blocking agents, R will preferably be alkylene, e.g., lower ($C_1$–$C_6$) alkylene, including branched and linear forms as well as substituted and unsubstituted forms, or substituted or unsubstituted arylene, and R' similarly will preferably be alkyl, e.g., lower alkyl, or aryl.

The predetermined ratio of the activating and blocking agents is established with excess amounts of each. By this is intended that the respective amounts of the activating and blocking agent present in the reaction mixture is in excess of that which would result under the conditions of reaction in the covalent linking of all of such agent. It will be preferred to operate in substantial excess of such amount, usually greater than 2-fold excess, and more preferably greater than 10-fold excess, up to as much as 100-fold excess or greater.

A particularly preferred polymer/activating agent/blocking agent system involves poly(aspartic acid) as the polymer base. In the closed ring form as polysuccinimide, this polymer is a homopolymer of repeating monomeric units having a derivatizable carboxyl functionality. The activating and blocking agents are an alkyldiamine and an alkylmonoamine, respectively, wherein alkyl is defined as above.

Preferred alkyldiamine activating agents are oxaalkane diamines having from about 2 to about 20 alkylene groups, for example, of the formula:

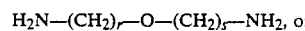

$H_2N-(CH_2)_r-O-(CH_2)_s-NH_2$, or

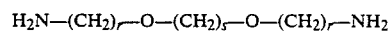

$H_2N-(CH_2)_r-O-(CH_2)_s-O-(CH_2)_r-NH_2$ wherein r and s, respectively, are integers from 2 through 20 and can be the same or different integer. By oxaalkane will be understood a linear chain of two or more alkylene groups linked together by oxygen as an ether linkage. The alkylene groups can be substituted, but preferably are unsubstituted, and can comprise up to as many as 20 alkylene units such as ethylene, propylene, hexylene, and so forth. The repeating alkylene units can be all the same, some the same, or all different along the chain in terms of length and any substituents.

Preferred alkylmonoamine blocking agents are aminoalkanols having from about 2 to about 10 alkylene groups, and include aminoethanol, aminopropanol, aminohexanol, and the like. The hydroxyl functionality introduced by coupling of such a blocking agent to the polymer is unreactive in the coupling reactions typically used to link to amino groups, as introduced by the preferred activating agents, and imparts hydrophilic character to assist in maintaining water solubility of the polymer.

The coupling of the desired ligand to the functional group introduced by derivatization of the polymer with the activating agent can be accomplished in any desired manner. It can be desirable, but is not required, that the activating agent be selected to have a functional group that is reactable directly with a desired functionality on the ligand. Alternatively, the coupling can involve conventional homo- or hetero bifunctional linking agents and/or preliminary derivatization of the ligand to introduce a couplable functionality or linking arm. Following are representative ligand-coupling schemes.

1. Coupling of a carboxylic functionalized ligand with an amino functionalized polymer using a condensation reagent such as 1-ethyl-3(-3-dimethyl-amino propyl)-carbodimide HCl [Previero et al. FEBS letter 33:135 (1973)].

2. Coupling of an active carboxylic ester (active ester of carboxylic acid and N-hydroxysuccinimide) of the functionalized ligand with an amino functionalized polymer. [Anderson. G. W. et al. J. Am. Chem. Soc. 86:1839 (1964)].

3. Coupling of a sulfhydryl functionalized ligand with an active halide (iodoacetyl) functionalized polymer. [Sutoh, K. et al. J. Mol. Biol. 178:323 (1984)].

4. Coupling of a sulfhydryl functionalized ligand with a maleimido functionalized polymer. [Kitagawa, T. et al. J. Biochem 79:233 (1976)].

5. Coupling of an acyl chloride functionalized ligand with a hydroxyl functionalized polymer.

6. Coupling of an aldehyde functionalized ligand with a hydrazido functionalized polymer. [Heitzmann et al Proc. Natl. Acad. Sci. U.S.A. 71:35-37 (1974)].

The ligand to be coupled to the derivatized polymeric material will be understood to be essentially any organic molecule of interest which has a specific binding partner, and will usually have a molecular weight between about 50 and as high as 200,000 daltons, but commonly will be smaller than 100,000 daltons. Since the present invention is particularly designed for preparing an analytical reagent, the ligand will normally be a substance of analytical interest or related by binding interactions to an analyte of interest, e.g., will be a binding partner to the analyte or a binding analog to the analyte, that is, will be bindable by the same binding partner as the analyte. The binding partner for the ligand can be a binding protein, nucleic acid, or the like, and usually will be selected from one of the members of the following types of binding pairs: haptens/antibodies; antigens/antibodies; hormones, vitamins, metabolites/receptors; biotin/avidin; carbohydrates/lectins; complementary polynucleotides; and nucleic acid/protein interactions.

The present invention is particularly useful for the coupling of small organic bindable substances having molecular weights between about 100 and about 2,000 daltons, such as haptens and biotin. Haptens can be represented, without limitation, by drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, netilmicin, penicillin, tetracycline, terramycin, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, amphetamines, catecholamines, and antihistamines. The haptenic ligand can also be a synthetic or digested fragment of an antigen which comprises an epitope of diagnostic significance, e.g., a peptide residue which is modified or unmodified, for instance, the glycated peptides characteristic of glycated proteins such as hemoglobin Alc.

The product of the present method will have its principal use as a reagent in a binding assay involving the coupled ligand, particularly immunoassays. For example, where the polymer base is a solid macrosupport such as a bead or reaction vessel surface, the ligand can participate in competitive and noncompetitive immunoassays for determining a binding partner for the ligand, e.g., antibody, or a binding analog of the ligand. The present reagent can be employed essentially in any binding assay wherein assay performance is affected by the ability to control the density of ligand on a polymer support material.

A particularly important use of the present invention is to provide a reproducible water soluble or water suspensible agglutinator reagent for use in agglutination-based immunoassay. Such assays are based on measurement of turbidity formed by agglutination between (i) a multivalent antibody reagent comprising an anti-analyte antibody, or a fragment thereof, bound to a water suspensible particle, and (ii) an agglutinator reagent being multiple ligands and prepared according to the present invention wherein the coupled ligand comprises an epitopic binding site for the anti-analyte antibody or fragment, e.g., the ligand is the analyte or an analog thereof capable of being bound by the anti-analyte antibody or fragment. Quantitation is achieved by turbidimetric measurement and comparison to standard results. The use of an agglutinator reagent prepared according to the present invention provides improved precision and sensitivity and decreased reaction times.

The present invention will now be illustrated, but is not intended to be limited, by the following examples.

EXAMPLES

Referring to FIG. 1 of the drawing, aspartic acid was polymerized to polysuccinimide (I). The polymer was then reacted with a mixture of alkyl-monoamine and alkyl-diamine to form an amino functionalized poly(aspartic) acid (II). The amino group was further functionalized with 4-(maleimidomethyl)-1-cyclohexanecarboxylic acid-N-hydroxy-succinimide ester (SMCC) to generate a maleimido functionalized poly(aspartic) acid. The sulfhydryl group of a glycated peptide (Glc-peptide) was then allowed to react with the maleimido functionalized poly(aspartic) acid to give the multi-Glc-peptide-poly(aspartic) acid (III). The material so prepared was found to cause anti-Glc-peptide antibody coated latex to agglutinate and therefore to be useful in an immunoassay.

Aspartic acid, aminoethanol, SMCC, 4,9-dioxa-1,12-dodecanediamine and dimethylformide (DMF) were obtained from Aldrich Chemical Co., Inc., Milwaukee, Wis., USA.

A. Preparation of poly(aspartic acid) (I).

This polymer was prepared according to the procedure of Alpert, J. Chromatography 266:23(1983).

B. Preparation of amino-functionalized polymer (II).

Aminoethanol and 4,9-dioxa-1,12-dodecanediamine were dissolved in DMF under argon. The solution was treated with a solution of poly(aspartic acid) and DMF. The reaction was stirred at room temperature for 1 hour and then 70° C. for 2 hours. The mixture was then cooled and most of the liquid was removed by evaporation under reduced pressure. The oily residue was washed repeatedly with ether and then warm tetrahydrofuran. The product was solidified and recovered by filtration. The crude product was dissolved in water and the pH was adjusted to neutral. The solution was then purified with a BioRad P6-DG desalting gel column (BioRad Laboratories, Richmond, Calif., USA). Fractions containing the compound (II) were pooled and lyophilized.

The number of amino groups on the polymers was determined by Habeeb's TNBS assay [Anal. Biochem. 14:328–336(1966)]. Results are shown in Table 1.

TABLE 1

| | Preparations | | |
|---|---|---|---|
| | A | B | C |
| Amount of reactant | | | |
| Polymer (mmoles) | 10 | 10 | 10 |
| Aminoethanol (mmoles) | 90 | 80 | 50 |
| 3,4,3-Diamine (mmoles) | 10 | 20 | 50 |
| Amino groups per mg polymer | | | |
| Calculated | 13 | 26 | 65 |
| Actual | 11.7 | 22 | 36.7 |

The data demonstrate that the amount of amino groups on the polymer can be controlled by varying the ratio of the alkyl monoamine blocking agent and the alkyl diamine activating agent.

C. Preparation of multi-Glc-peptide-poly(aspartic acid( III).

Amino functionalized poly(aspartic acid) and SMCC were dissolved in DMF. The reaction was allowed to stir at room temperature for 2 hours. Ice water was added to the mixture and the activated polymer was separated from the mixture with a BioRad 6P-DG gel column. The activated polymer was then allowed to react at room temperature for 3 minutes with the glycated peptide 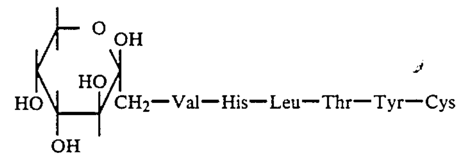 prepared according to the methods described in European Patent Publication No. 185,870. After the reaction, the product (III) was again purified with a 6P-DG gel column and lyophilized.

The number of maleimido groups on the activated polymers was determined by the PDS assay [Grassetti and Murray, Arch. Biochem. Biophys. 119:44–49(1967)]. The amount of Glc-peptide on the polymers was determined by UV/Vis absorption measurement using 275 nm as the molar extinction coefficient for tyrosine. Results are shown in Table 2.

The data show that the number of ligands (Glc-peptide) coupled to the polymer can be controlled by the amount of amino groups on the polymer and the concentration of the other reactants.

TABLE 2

| | Preparation | | | | |
|---|---|---|---|---|---|
| | A' | B' | C' | D' | E' |
| Amount of reactant | | | | | |
| Amino-polymer (mg) | 20 | 20 | 20 | 20 | 10.7 |
| Amino groups per mg polymer | 11.7 | 11.7 | 11.7 | 11.7 | 22 |
| SMCC (mg) | 15 | 25 | 25 | 28.5 | 30 |
| Glc-peptide (mg) | 0.1 | 5.2 | 10.4 | 20 | 20 |
| Maleimide groups per polymer (μmole/mg) | 0.15 | 0.15 | 0.15 | 0.29 | 0.46 |
| Glc-peptide per polymer (μmole/mg) | 0.02 | 0.093 | 0.19 | 0.26 | 0.46 |
| Glc-peptide/polymer (mole ratio) | 0.4 | 1.9 | 3.8 | 5.2 | 9.4 |

D. Latex agglutination reaction

Solutions containing 1.25, 2.5, 5, 10, 20, and 40 μg/mL of compound (III) from each of Preparations A'-E' in phosphate buffer (20 mM, pH=6.0, 0.1% BSA, 0.1% $NaN_3$) were prepared. The solutions were used as agglutinators. A 25 μL aliquot of the agglutinator solution was added to a mixture of 0.5 mL of latex coated with antibody to hemoglobin Alc (see European Patent Publication No. 185,870) and 10 μL of a mixture of 3M $NH_4SCN$ and 2 mg/ml $K_3Fe(CN)_6$. The absorption (A) of each reaction at 540 nm was measured after 20 minutes at room temperature. The absorption of antibody-coated latex (Al) without the agglutinator was also measured.

$$\text{Agglutination} = (A/Al) \times 100$$

The results of agglutination reactions with different agglutinators are shown in FIGS. 2 and 3 of the drawing.

FIG. 2 shows the relationship between the measured agglutination and the amount of various agglutinators in the reaction mixture. The amount of Glc-peptide per mg polymer in the agglutinator is indicated on FIG. 2 next to the respective curves.

FIG. 3 shows the relationship between the Glc-peptide/polymer ratio and maximum observed agglutination. The data show that reproducible maximum agglutinations are dependent upon the controlled number of ligand residues on the polymer.

E. Comparison to Prior Art

A Glc-peptide-BSA conjugate was prepared, optimized and used in the latex agglutination immunoassay.

Bovine serum albumin (BSA, Sigma Co., St. Louis, Mo. U.S.A., 50 mg, 0.72 μmoles, 44 μmoles-NH$_2$ groups) was mixed with 4.5 mL phosphate buffer (100 mM, pH=7.0 and 1 mM EDTA). The solution was treated with a solution of SMCC (50 mg, 150 μmoles) dissolved in 0.5 ml dimethylformamide (DMF). The mixture was allowed to react at room temperature for 30 minutes. The reaction mixture was applied to a Sephadex G-25 column (2.5 ×28 cm, Pharmacia Fine Chemicals, Piscataway, N.J. U.S.A.), equilibrated with 100 mM phosphate buffer, pH=6.0 and 1 mM EDTA. The first peak collected was found to contain the maleimido-activated BSA. The number of maleimido groups on the activated BSA can be determined by the PDS assay. The activated BSA was then allowed to react at 4° C. with the Glc-peptide, supra (5 mg), for 40 hours. The product was again purified by Sephadex G-25 chromatography. The amount of Glc-peptide linked to BSA was determined by the fructoseamine assay [(Johnson et al, Clin. Chem. Acta 127:87(1982)]. The Glc-peptide-BSA conjugate was used in place of compound (III) as the agglutinator reagent in the latex agglutination immunoassay described above.

When BSA was used as the polymeric material in the agglutinator reagent, only 5-10 of the amino groups (out of the possible 61 groups) on the BSA were capable of being functionalized. This conjugate was found to give an agglutination response equivalent to the present compound (III) having a density of 0.19-0.21 μmole Glc-peptide per mg polymer. This inferior performance is apparently due to the inaccessibility of the other NH$_2$ groups on BSA.

The present invention has been particularly described and exemplified above. Obviously, many other variations and modifications of the invention can be made without departing from the spirit and scope hereof.

What is claimed is:

1. A method for chemically coupling a reproducible number of ligands to a polymeric material, comprising the steps of:
   (a) reacting a polymeric material having a repeating functional group to introduce a reproducible proportion of a second functional group by reacting the polymeric material with a mixture of a predetermined ratio of excess amounts of (1) an activating agent which is reactive with said repeating functional group to form a covalent bond thereto and which comprises said second functional group, and (2) a blocking agent which also is reactive with said repeating functional groups to form a covalent bond thereto but which does not comprise said second functional group, and
   (b) covalently coupling said ligands to the polymeric material through the introduced second functional groups.

2. The method of claim 1 wherein the ligands are substances which ave a specific protein binding partner.

3. The method of claim 2 wherein the ligands are haptens or biotin.

4. The method of claim 1 wherein the chemical group that reacts to form a covalent bond with the repeating functional group on the polymeric material is the same in both the activating and blocking agents.

5. The method of claim 4 wherein the reactive group common to both the activating and blocking agents is an amine group and the repeating functional group on the polymeric material is a carboxyl group, whereby covalent peptide bonds are formed therebetween.

6. A method for preparing a multivalent hapten-polymer conjugate having a reproducible number of hapten moieties coupled to the polymer, which method comprises the steps of:
   (a) reacting poly(aspartic acid) with a mixture of a predetermined ratio of excess amounts of a diamine and a monoamine under conditions favorable to the formation of a covalent bond between the repeating carboxyl groups on poly(aspartic acid) and the amine groups on said diamine and monoamine, and
   (b) covalently coupling the hapten to the derivatized poly(aspartic acid) through the amine functional groups introduced by reaction with the diamine.

7. The method of claim 6 wherein the diamine and monoamine are an alkyldiamine and an alkylmonoamine, respectively.

8. The method of claim 7 wherein the alkyldiamine is an oxaalkanediamine having from about 2 to about 20 alkylene groups.

9. The method of claim 8 wherein the alkylmonoamine is an aminoalkanol having from about 2 to about 10 alkylene groups.

10. The method of claim 6 wherein the hapten is coupled to the introduced amine groups on poly(aspartic acid) through a bifunctional coupling agent.

11. The method of claim 6 wherein the poly(aspartic acid) is water soluble and has a molecular weight of between about 500 and about 500,000 daltons.

12. The product prepared by the method of any one of claims 1-11.

* * * * *